United States Patent [19]

Kelley

[11] Patent Number: 5,095,018

[45] Date of Patent: Mar. 10, 1992

[54] 3-BENZYL-1,2,4-TRIAZOLO[4,3-a] PYRAZINES

[75] Inventor: James L. Kelley, Raleigh, N.C.

[73] Assignee: Burroughs Wellcome Co., Research Triangle Park, N.C.

[21] Appl. No.: 674,435

[22] Filed: Mar. 22, 1991

Related U.S. Application Data

[63] Continuation of Ser. No. 533,604, Jun. 5, 1990, abandoned.

[30] Foreign Application Priority Data

Jun. 6, 1989 [GB] United Kingdom ............ 8913011.6

[51] Int. Cl.$^5$ ................... A61K 31/495; C07D 487/04
[52] U.S. Cl. ..................................... 514/249; 544/350
[58] Field of Search ..................... 544/350; 514/249

[56] References Cited

U.S. PATENT DOCUMENTS 3,629,260 12/1971 Maguire et al. ..................... 544/350
4,056,632 11/1977 Mehta et al. .
4,438,266 3/1984 Hartman .............................. 544/350

FOREIGN PATENT DOCUMENTS

0157637A2 10/1985 European Pat. Off. .
0166609 1/1986 European Pat. Off. ............ 544/350
48-43519 12/1973 Japan .................................. 544/350
1561072 2/1980 United Kingdom .

OTHER PUBLICATIONS

Schneller, et al., J. Heterocyclic Chem., 15, pp. 987–992, Sep. 1978, Formycin Analogs. I. Model Studies in Preparation of an Isomer of Formycin and Related Derivatives (s-Triazolo[4.3-a]pyrazines).

Kelley, et al., J. Heterocyclic Chem., 25, pp. 1255–1258, Jul.-Aug. 1988, Synthesis and Anticonvulsant Activity of 1-Benzyl-4-Alkylamino-1H-Imidazo[4,5-c]pyridines.

Adachi, et al., J. Org. Chem., vol. 37, No. 2, 1972, pp. 221–225, Studies on Pyrazines. I. The Syntheses of 2,3-Dihydroxyprazines and Their Derivatives.

Woodbury, et al., Arch. int. pharmacodyn., 1952, XCII, No. 1, pp. 97–107, Design and Use of a New Electroshock Seizure Apparatus, and Analysis of Factors Altering Seizure Threshold and Pattern ([1]).

Huynh-Dinh, et al., J. Org. Chem., vol. 44, No. 7, 1979, pp. 1028–1035, Synthesis of C-Nucleosides. 17[1]s--Triazolo [4,3-a]pyrazines[2].

*Primary Examiner*—Donald G. Daus
*Attorney, Agent, or Firm*—Donald Brown; Lawrence A. Nielsen

[57] ABSTRACT 3-benzyl-1,2,4-triazolo [4,3-a] pyrazines are prepared. They are useful as anticonvulsants.

23 Claims, No Drawings

3-BENZYL-1,2,4-TRIAZOLO[4,3-a] PYRAZINES

This is a continuation of copending application Ser. No. 533,604, filed on Jun. 5, 1990, now abandoned.

The present invention relates to a class of 1,2,4-triazolo[4,3-a]pyrazine compounds, to pharmaceutical compositions containing them, to methods for their preparation and to methods of treating epilepsy in mammals.

European Patent Application No. 85302321.6, published under No. 157637 discloses a class of 6-amino-9-(fluorobenzyl)-9H-purines as having anticonvulsant activity. 3-Deazapurines have also been reported (J.Heterocyclic Chem, 25. 1255 (1988)) to have anticonvulsant activity.

Epilepsy is a collective designation for a group of chronic central nervous system disorders having in common the occurrence of sudden and transitory episodes (seizures) of abnormal phenomena of motor (convulsions), sensory, autonomic or psychic origin. The seizures are nearly always correlated with abnormal electrical activity of the brain.

The incidence of epilepsy is estimated to be approximately 1% of the total world population. A fairly large proportion (10%-20%) is not adequately controlled by currently available therapies; such patients are described as refractory. Those drugs which are currently available to the medical practitioner suffer from severe limitations in use and also have a number of side effects. It is therefore clearly apparent that there is a need for new antiepileptic drugs.

The present invention is directed to a series of novel 1,2,4-triazolo-[4,3a]pyrazines which have potent anticonvulsant activity.

Accordingly in a first aspect of the present invention there is provided a compound of formula I

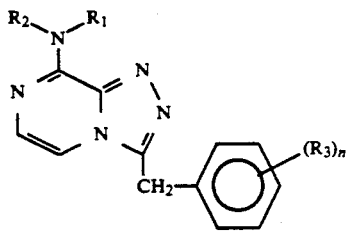

(I)

or a salt(preferably a pharmaceutically acceptable salt) thereof wherein $R_1$ and $R_2$ may be the same or different and are selected from hydrogen, $C_{1-4}$ straight or $C_{3-4}$ branched alkyl, $C_{3-4}$ cycloalkyl or cyclopropylmethyl; $R_3$ is hydrogen, or halo, preferably fluoro; and n is 1 or 2.

Preferred compounds and salts thereof are those wherein $R_3$ is fluoro; more preferred are those wherein $R_3$ is selected from 2-fluoro; 3-fluoro; 4-fluoro; 2,6-difluoro; 2,5-difluoro; 2,4-difluoro; 2,3-difluoro; 3,4-difluoro and 3,5-difluoro. Also preferred is the compound wherein $R_3$ is hydrogen.

The following compounds and their salts (preferably pharmaceutically acceptable acid addition salts) are particularly preferred:
3-Benzyl-8-(methylamino)-1,2,4-triazolo[4,3-a]pyrazine,
3-(2-fluorobenzyl)-8-(methylamino)-1,2,4-triazolo[4,3-a]pyrazine,
8-amino-3-(2-fluorobenzyl)-1,2,4-triazolo[4,3-a]pyrazine,
3-(3-fluorobenzyl)-8-(methylamino)-1,2,4-triazolo[4,3-a]pyrazine,
3-(4-fluorobenzyl)-8-(methylamino)-1,2,4-triazolo[4,3-a]pyrazine,
3-(2,5-difluorobenzyl)-8-(methylamino)-1,2,4-triazolo[4,3-a]pyrazine,
8-amino-3-(2,5-difluorobenzyl)-1,2,4-triazolo[4,3-a]pyrazine,
3-(2,6-difluorobenzyl)-8-(methylamino)-1,2,4-triazolo[4,3-a]pyrazine,
8-amino-3-(2,6-difluorobenzyl)-1,2,4-triazolo[4,3-a]pyrazine,
8-(cyclopropylamino)-3-(2,6-difluorobenzyl)-1,2,4-triazolo[4,3-a]pyrazine,
8-(cyclopropylamino)-3-(2-fluorobenzyl)-1,2,4-triazolo[4,3-a]pyrazine, Suitable acid addition salts of the compounds of formula I include those formed with both organic and inorganic acids. Such acid addition salts will normally be pharmaceutically acceptable.

Thus, preferred salts include those formed from hydrohalic, e.g., hydrochloric, sulfuric, citric, isethionic, tartaric, phosphoric, lactic, pyruvic, acetic, succinic, fumaric, maleic, lactobionic, oxaloacetic, methanesulphonic, p-toluenesulphonic and benzenesulphonic acids.

There is also provided the first medical use of the novel compounds of the present invention or pharmaceutically acceptable salts thereof, as hereinbefore defined. Preferably this will be for the treatment of epilepsy, e.g., in mammals such as humans. The compounds of the present invention have phenytoin like activity and are particularly useful in the treatment of primary generalized tonic-clonic (grand mal) epilepsy.

In a further aspect, there are provided pharmaceutical formulations comprising a compound of the present invention in admixture with a pharmaceutically acceptable carrier therefor.

The pharmaceutically acceptable carriers present in the compositions of this invention are materials recommended for the purpose of administering the medicament. These may be liquid or solid materials, which are otherwise inert or medically acceptable and are compatible with the active ingredients.

These pharmaceutical compositions may advantageously be given orally, but may also be given parenterally, used as a suppository, or applied topically as an ointment, cream or powder. Oral and parenteral administration of the compositions are preferred.

For oral administration, fine powders or granules will contain diluting, dispersing and/or surface active agents, and may be presented in a draught, in water or in a syrup, in capsules or sachets in the dry state or in non-aqueous suspension wherein suspending agents may be included, or in a suspension in water or syrup. Where desirable or necessary, flavoring, preserving, suspending, thickening or emulsifying agents can be included.

For parenteral administration, the compounds may be presented in sterile aqueous injection solutions which may contain anti-oxidants or buffers.

As stated above, the free base or a pharmaceutically acceptable salt thereof may be administered in its pure form unassociated with other derivatives, in which case a capsule or sachet is the preferred carrier.

Alternatively the active compound may be presented in a pure form as an effective unit dosage, for instance compressed as a tablet or the like.

Other compounds which may be included are, for example, medically inert ingredients, e.g., solid and liquid diluents such as lactose, starch or calcium phosphate for tablet or capsule; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Tablets or other forms of presentation provided in discrete units may conveniently contain an amount of a novel compound as hereinbefore defined which is effective at such dosage or a multiple of the same, for instance, units containing 5 mg to 500 mg, usually around 10 mg to 250 mg.

The pharmaceutical compositions of the present invention will be prepared by the admixture of a novel compound or salt as hereinbefore defined with a pharmaceutically acceptable carrier. Conventional pharmaceutical excipients may be admixed as required.

The present invention provides a method of treatment of CNS disorders, such as convulsions particularly epilepsy, in mammals, by the administration of a non-toxic therapeutically effective amount of a compound of the formula I or a pharmaceutically acceptable salt, or a composition as hereinbefore defined.

Preferably the mammal is a human.

Before commencement of the treatment the mammal il question will, in general, have been identified as suffering from a CNS disorder, particularly epilepsy.

Thus in a preferred embodiment of the present invention, there is provided a method of treatment of epilepsy in humans, comprising the administration to a human in need thereof of a non-toxic therapeutically effective amount of a compound of the formula I or a pharmaceutically acceptable salt thereof, or a composition as hereinbefore defined.

As indicated above, the compounds of the formula I are generally useful in treating such disorders by administration to the human or animal recipient by a route selected from oral, parenteral (including subcutaneous, intradermal, intramuscular and intravenous) and rectal. The size of an effective dose of a compound will depend upon a number of factors including the mammal under treatment (for example cat, dog or human), the type of epilepsy involved for example grand mal, focal seizures and psychomotor convulsions, the severity of the condition to be treated and the route of administration, and will ultimately be at the discretion of the attendant physician. In guiding him in assessing the efficacy and acceptability of a regimen the physician will have recourse to changes in the recipient's gross condition as treatment progresses.

Such an effective dose for the treatment of epilepsy will generally be in the range 0.1 to 15 mg/kg bodyweight of animal or human recipient given three times per day, preferably in the range 0.25 to 7 mg/kg bodyweight and most preferably in the range of 0.5 to 2 mg/kg bodyweight. For the average human of 70 kg bodyweight at 1.0 mg/kg the dose would be 70 mg. Unless otherwise indicated all weights are calculated as the hydrochloride of a compound of formula I. For other salts the figures would be amended proportionately. The desired dose may be preferably presented as from two to four sub-doses administered at appropriate intervals throughout the day.

The present invention also provides a process for producing compounds of formula I, which process comprises the reaction of an amine $HNR_1R_2$ with a compound of formula II

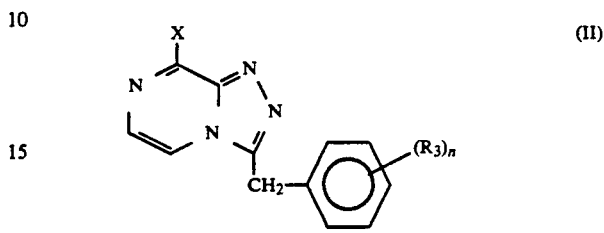

wherein X is a leaving group, and $R_1$, $R_2$ and $R_3$ and n are as hereinbefore defined. Preferably the reaction takes place in a polar aqueous solvent such as $C_{1-4}$ alkanol (preferably ethanol), water or acetonitrile. Other solvents such as DMF, ethers and the like will also be suitable. Where appropriate, the amine may be used as co-solvent. The reaction may be carried out from $-20$ to $100°$ C., but is conveniently carried out at ambient temperatures.

Suitable leaving groups include halogen, $C_{1-6}$alkythio, $C_{6-10}$arylthio, $C_{7-12}$aralkylthio or $C_{1-4}$alkyl-, phenyl-, benzyl-, phenylethyl- or napthylmethyl-substituted sulphonyl or sulphinyl. Particularly preferred leaving groups include halogen, particularly chlorine.

Compounds of formula II are prepared by the condensation of a compound of formula III

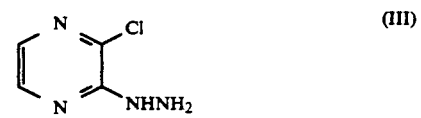

with a compound of formula IV

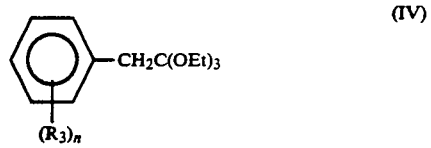

wherein $R_3$ and n are hereindefined.

This reaction preferably occurs at reflux in an organic solvent, e.g., xylene.

Compounds of formula III can be prepared from the known 2,3-(1H,4H)-pyrazinedione (J.Org.Chem. 1972, 37, (2), 221),

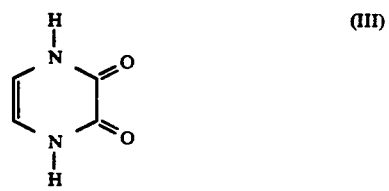

by chlorinating with phenylphosphonic dichloride at 160° C. followed by subsequent reaction of the resulting 2,3-dichloropyrazine with hydrazine hydrate in ethanol at ambient temperatures.

Compounds of formula IV may be prepared from compounds of formula V,

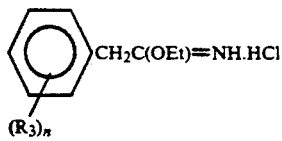

wherein $R_3$ and n are as hereindefined, by reacting with absolute ethanol.

Compounds of formula V may be prepared from the respective substituted benzyl cyanide, by reaction with hydrochloric acid in ethanol at 0° C.

The following examples serve to illustrate the present invention, but should not be construed as a limitation thereof.

EXAMPLE 1

Preparation of 3-(2-fluorobenzyl)-8-(methylamino)-1,2,4-triazolo4,3-a]pyrazine hydrochloride A) Preparation of 1-fluoro-2-(2,2,2-triethoxyethyl)benzene Dry hydrogen chloride gas (29.8 g, 0.817 mol) was bubbled through a solution of 2-fluorophenylacetonitrile (100 g, 0.743 mol) (Aldrich) in absolute ethanol (37.6 g, 0.817 mol) at 0° C. After uptake of hydrogen chloride was complete, the reaction was kept at 0° C. for 48 hours. The solid was triturated in ether (3×200 mL) and the white solid was collected by suction filtration. Drying for several days under vacuum in a desiccator containing sodium hydroxide pellets and phosphorus pentoxide gave 148 g (91%) of ethyl 2-(2-fluorophenyl)acetimidate hydrochloride, mp. 96°–99° C.; nmr (DMSO-d$_6$)L $\delta$11.58 (br s, 2H, NH2), 6.95–7.50 (complex multiplets, 4H, ArH), 4.40 (q, 2H, OCH$_2$), 4.06 (s, 2H, CH$_2$), 1.24 (t, 3H, CH$_3$); ms: m/e 181 (M+), 162 (M-F+), 153 (M-C$_2$H$_4$+), 136 (M-OEt+), 109 (C$_7$H$_6$F+).

Anal. Calcd for C$_{10}$H$_{13}$ Cl F N O: C, 55.18; H,6.02; N,6.43. Found: C,54.43; H,6.07; N,6.57.

A mixture of ethyl 2-(2-fluorophenyl)acetimidate hydrochloride (34.4 g, 0.158 mol) and absolute ethanol (50 mL) was stirred at ambient temperature for 18 hours. Diethyl ether (50 mL) was added to the mixture, and the solids were removed by suction filtration. The solids were rinsed with ether (2×25 mL), and the combined filtrates were spin evaporated in vacuo to give 34.7 g (86%) of 1-fluoro-2-(2,2,2-triethoxyethyl)benzene as a semisolid; nmr (DMSO-d$_6$): $\delta$6.7–7.7 (complex multiplets, 4H, ArH), 3.48 (q, 6H, OCH$_2$), 3.03 (s, 2H, CH$_2$), 1.03 (t, 9H, CH$_3$).

B) Preparation of 3-benzyl-8-chloro-1,2,4-triazolo[4,3-a]pyrazine

2-Chloro-3-hydrazinopyrazine was prepared in four steps. The procedure of J. Adachi and N. Sato, J.Org.-Chem. 37, 221 (1972) was used to prepare 2,3(1H,4H)-pyrazinedione in two steps, followed by chlorination and reaction of the dichloropyrazine with hydrazine as described in S. W. Schneller and J. L. May, J.Het.-Chem. 15,987 (1978). A mixture of 2-chloro-3-hydrazinopyrazine (8.51 g, 58.9 mmol), 1-fluoro-2-(2,2,2-triethoxyethyl)benzene from 1(A) (34.7 g, 135 mmol) and xylene (125 mL) (dried over calcium chloride) was refluxed for 3 hours. The solvent was removed by spin evaporation in vacuo. The solid residue was triturated in ether (200 mL) and the solid was collected by suction filtration. The solid was rinsed with ether and dried with aspirator suction to give 14.9 g (96%) of crude 3-benzyl-8-chloro-1,2,4-triazolo[4,3-a]pyrazine. Recrystallisation of 1.0 g of crude 3-benzyl-8-chloro-1,2,4-triazolo[4,3-a]pyrazine from ethanol:water gave 0.697 g of the analytically pure product, mp. 126°-127° C.; UV (0.1 N hydrochloride acid+10% ethanol): $\lambda$max 300 nm ($\epsilon$4200); (pH 7.0 buffer+10% ethanol): $\lambda$max 300 nm ($\epsilon$4300); nmr(DMSO-d$_6$) $\delta$8.58 (d, 1H, J=4.7 Hz, H-5 or H-6), 7.79 (d, 1H, J=4.7 Hz, H-5 or H-6), 7.09–7.40 (complex multiplets, 4H, ArH), 4.60 (s, 2H, CH$_2$); ms: m/e 262 (M+), 261 (M-1+), 243 (M-F+), 227 (M-Cl+), 109 (C$_7$H$_6$F+).

Anal. Calcd for : C,54.87; H,3.07; N,21.33. Found: C,54.96; H,3.08; N,21.29.

C) Preparation of 3-(2-fluorobenzyl)-8-(methylamino)-1,2,4-triazolo-[4,3-a]pyrazine hydrochloride 40% aqueous methylamine (50 mL) was added to a mixture of 3-benzyl-8-chloro-1,2,4-triazolo[4,3-a]pyrazine (4.00 g, 15.2 mmol) and ethanol (60 mL). After stirring for 1.5 hours the mixture was suction filtered, and the solid was dried to give 3.31 g (85%) of crude 3-(2-fluorobenzyl)-8-(methylamino)-1,2,4-triazolo [4,3-a]pyrazine. Recrystallization of the solid from ethyl acetate/hexane gave 2.57 g(66%) of 3-(2-fluorobenzyl)-8-(methylamino)-1,2,4-triazolo[4,3-a]-pyrazine as the analytically pure product, mp. 165°–167° C., UV (0.1 N hydrochloric acid+10% ethanol): $\lambda$max 232 nm ($\epsilon$27000); (pH 7.0 buffer+10% ethanol): $\lambda$max 236nm ($\epsilon$17000); (0.1 N sodium hydroxide+10% ethanol); $\lambda$max 236 nm ($\epsilon$16000).

Anal. Calcd for C$_{13}$H$_{12}$FN$_5$: C,60.69; H,4.70; N,27.22. Found: C,60.60; H,4.75; N,27.19.

Dissolution of 3-(2-fluorobenzyl)-8-(methylamino)-1,2-4-triazolo[4,3-a]pyrazine (2.45 g) in warm ethanol (175 mL) followed by addition of ethereal hydrogen chloride to the solution afforded a precipitate with cooling over ice. Collection of the solid by suction filtration gave 2.31 g (94% recovery) of the title compound as analytically pure material, mp 292°–295° C. (dec); nmr (DMSO-d$_6$); $\delta$10.07 (br s, 1H, NH), 7.83 (d, 1H, J=5.4 Hz, H-6 or H-5), 7.12–7.40 (complex multiplets, 5H, ArH and H-5 or H-6), 4.53 (s, 2H, CH$_2$), 3.07 (s, 3H, CH$_3$); ms: m/e 257 (M+), 229 ((M+1)-CH$_2$NH+), 121 (C$_8$H$_6$F+), 109 (C$_7$H$_6$F+).

Anal. Calcd for C$_{14}$H$_{13}$ClFN$_5$: C,53.16; H,4.46; N,23.84. Found: C,53.13; H,4.50; N,23.77.

EXAMPLE 2

Preparation of 8-amino-3-(2-fluorobenzyl)-1,2,4-triazolo[4,3-a]-pyrazine

This compound and its hydrochloride salt was prepared analogously manner to the compound of Example 1, using ammonia in place of methylamine in 1C. Mp. 289°–292° C. (dec) and 286°–289° C. (dec) (hydrochloride salt).

EXAMPLE 3

Preparation of
3-benzyl-8-(methtlamino)-1,2,4-triazolo[4,3-a]-pyrazine

This compound and its hydrochloride salt were prepared in a manner analogous to the compound in Example 1, replacing 2-fluorophenylacetonitrile in Example 1A with phenylacetonitrile (Aldrich). Mp. 178°–180° C. and 280°–282° C. (dec) HCL salt.

EXAMPLE 4

Preparation of
3-(3-fluorobenzyl)-8-(methylamino)-1,2,4-triazolo[4,3-a]-pyrazine This compound and its hydrochloride salt were prepared in a manner analogous to the compound in Example 1, replacing 2-fluorophenylacetonitrile in Example 1A with 3-fluorophenylacetonitrile (Aldrich): Mp. 167°–168° C. and >250° C. (hydrochloride salt).

EXAMPLE 5

Preparation of
3-(4-fluorobenzyl)-8-(methylamino)-1,2,4-triazolo[4,3-a]-pyrazine This compound and its hydrochloride salt were prepared in a manner analogous to the compound in Example 1, replacing 2-fluorophenylacetonitrile in Example 1A with 4-fluorophenylacetonitrile (Aldrich): Mp. 199°–201° C. and >250° C. (hydrochloride salt).

EXAMPLE 6

Preparation of
3-(2.5-difluorobenzyl)-8-(methylamino)-1,2,4-triazolo-[4.3-a]pyrazine This compound and its hydrochloride salt were prepared in a manner analogous to the compound in Example 1, replacing 2-fluorophenylacetonitrile in Example 1A with 2,5-difluorophenylacetonitrile (Aldrich): Mp. 192°–194° C. and >250° C. (hydrochloride salt).

EXAMPLE 7

Preparation of
8-amino-3-(2,5-difluorobenzyl)-1,2,4-triazolo[4,3-a]-pyrazine

This compound and its hydrochloride salt were prepared in a manner analogous to the compound in Example 2, replacing 2-fluorophenylacetonitrile in Example 1A with 2,5-difluorophenylacetonitrile (Aldrich): Mp.>250° C. and >250° C. (hydrochloride salt).

EXAMPLE 8

Preparation of
3-(2,6-difluorobenzyl)-8-(methylamino)-1,2,4-triazolo[4,3-a]pyrazine This compound and its hydrochloride salt were prepared in a manner analogous to the compound in Example 1, replacing 2-fluorophenylacetonitrile in Example 1A with 2,6-difluorophenylacetonitrile (Aldrich): Mp. 205°–207° C. and >250° C. (hydrochloride salt).

EXAMPLE 9

Preparation of
8-amino-3-(2,6-difluorobenzyl)-1,2,4-triazolo[4,3-a]pyrazine

This compound and its hydrochloride salt were prepared in a manner analogous to the compound in Example 2, replacing 2-fluorophenylacetonitrile in Example 1A with 2,6-difluorophenylacetonitrile (Aldrich): Mp. >250° C. and >250° C. (hydrochloride salt).

EXAMPLE 10

Preparation of
8-(cyclopropylamino)-3-(2,6-difluorobenzyl)-1,2,4-triazolo-[4,3-a]pyrazine This compound and its hydrochloride salt were prepared in a manner analogous to the compound in Example 1, replacing 2-fluorophenylacetonitrile in Example 1A with 2,6-difluorophenylacetonitrile (Aldrich) and replacing methylamine in Example 1C with cyclopropylamine (Aldrich): Mp. 186°–188° C. and 246°–256° C. (dec) (hydrochloride salt).

EXAMPLE 11

Preparation of
8-(cyclopropylamino)-3-(2-fluorobenzyl)-1,2,4-triazolo-[4,3-a]pyrazine This compound and its hydrochloride salt were prepared in a manner analogous to the compound in Example 1, replacing methylamino in Example 1C with cyclopropylamine (Aldrich): Mp. 143°–145° C. and 252°–260° C. (dec) (hydrochloride salt).

Pharmacological Activity

The anticonvulsant activity of certain compounds of the present invention were determined by a standard maximal electroshock test (MES); that described by L. A. Woodbury and V. D. Davenport, Arch. Int. Pharmacodyn, 1952, 92 95.

| COMPOUND OF EXAMPLE NO. | SALT | ED50.I.P. (mg/kg) | ED50.P.O. (mg/kg) |
|---|---|---|---|
| 1 | HCl | 4.1 | 8.3 |
| 2 | HCl | 9.4 | 8.0 |
| 3 | HCl | 6.2 | 15.6 |
| 4 | HCl | 4.1 | 20.4 |
| 5 | HCl | 25.0 | n.d. |
| 6 | HCl | 4.0 | 10.2 |
| 7 | HCl | 7.1 | 20.4 |
| 8 | HCl | 2.0 | 3.0. |
| 9 | HCl | 3.1 | 7.1. |
| 10 | HCl | 7.2 | n.d. |
| 11 | HCl | 9.4 | n.d. | n.d. = not determined

FORMULATION EXAMPLES

In the formulation examples that follow, the active ingredients are compounds hereinbefore defined by formula I.

| I - Formulation | |
|---|---|
| Compound | 25 mg |
| Corn starch | 45 mg |
| Polyvinylpyrrolidone | 6 mg |
| Stearic acid | 12 mg |
| Magnesium stearate | 2 mg |
| Lactose qs to | 300 mg |

The compound is finely ground and intimately mixed with the powdered excipients lactose and corn starch. The powders are wetted with a solution of polyvinylpyrrolidone dissolved in purified water and denatured alcohol to form granules. The granules are dried and mixed with the powdered stearic acid and magnesium stearate. The formulation is then compressed into tablets weighing approximately 300 mg each.

| II - Capsule | |
|---|---|
| Active ingredient | 25 mg |
| Corn starch | 45 mg |
| Stearic acid | 12 mg |
| Lactose qs to | 300 mg |

The finely ground active ingredient is mixed with the powdered exipients lactose and corn starch, and stearic acid and filled into hard-shell gelatin capsules.

| III - Suppository | |
|---|---|
| Active ingredient | 25 mg |
| Cocoa butter | 1975 mg |

The cocoa butter is heated to melting and the active ingredient is dispersed by thorough mixing. The mass is then formed into suppositories weighing approximately 2,000 mg each.

| IV - Injection | |
|---|---|
| Active ingredient | 25 mg |
| Sodium chloride | 0.9% |
| Preservative | 0.1% |
| Hydrochloric acid or sodium hydroxide as needed for pH adjustment | |
| Water for injection qs to | 2-3 ml. |

The active ingredient, sodium chloride, and preservative are dissolved in a portion of the water for injection. The pH of the solution is adjusted with hydrochloric acid or sodium hydroxide. Water for injection is added to final volume and the solution is thoroughly mixed. The solution is sterilized by filtration through a 0.22 micrometer membrane filter and aseptically filled into sterile containers.

| V - Syrup | |
|---|---|
| Active ingredient | 15 mg |
| Glycerin | 500 mg |
| Sucrose | 3500 mg |
| Flavoring agent | qs |
| Coloring agent | qs |
| Preserving agent | 0.1% |
| Purified water qs to | 5 ml |

The active ingredient and sucrose are dissolved in the glycerin and a portion of the purified water. The preserving agent is dissolved in another portion of hot purified water, and then the coloring agent is added and dissolved. The two solutions are mixed and cooled before the flavoring agent is added. Purified water is added to final volume. The resulting syrup is thoroughly mixed.

What I claim is:

1. A compound of the formula I wherein $R_1$ and $R_2$ may be the same of different and are selected from hydrogen, $C_{1-4}$ straight or $C_{3-4}$ branched alkyl, $C_{3-4}$ cycloalkyl or cyclopropylmethyl; $R_3$ is hydrogen, or halo, and n is 1 or 2; or a pharmaceutically acceptable salt thereof.

2. The compound of claim 1 wherein the salt is a pharmaceutically acceptable salt.

3. The compound of claim 2 wherein the salt is the pharmaceutically acceptable acid addition salt.

4. The compound of claim 3 wherein the salt is the hydrochloric salt.

5. A compound of claim 1 which is selected from 3-benzyl-8-(methylamino)-1,2,4-triazolo[4,3-a]pyrazine, 3-(2-fluorobenzyl)-8-(methylamino)-1,2,4-triazolo[4,3-a]pyrazine,
8-amino-3-(2-fluorobenzyl)-1,2,4-triazolo[4,3-a]pyrazine,
3-(3-fluorobenzyl)-8-(methylamino)-1,2,4-triazolo[4,3-a]pyrazine, 3-(4-fluorobenzyl)-8-(methylamino)-1,2,4-triazolo[4,3-a]pyrazine,
3-(2,5-difluorobenzyl)-8-(methylamino)-1,2,4-triazolo[4,3-a]pyrazine,
8-amino-3-(2,5-difluorobenzyl)-1,2,4-triazolo[4,3-a]pyrazine,
3-(2,6-difluorobenzyl)-8-(methylamino)-1,2,4-triazolo[4,3-a]pyrazine,
8-amino-3-(2,6-difluorobenzyl)-1,2,4-triazolo[4,3-a]pyrazine,
8-(cyclopropylamino)-3-(2,6-difluorobenzyl)-1,2,4-triazolo-[4,3-a]pyrazine, and
8-(cyclopropylamino)-3-(2-fluorobenzyl)-1,2,4-triazolo-4,3-a]pyrazine, or a pharmaceutically acceptable acid addition salt thereof.

6. A compound of claim 5 wherein the salt is the hydrochloride salt.

7. A pharmaceutical formulation comprising a compound of formula I wherein $R_1$ and $R_2$ may be the same or different and are selected from hydrogen, $C_{1-4}$ straight or $C_{3-4}$ branched alkyl, $C_{3-4}$ cycloalkyl or cyclopropylmethyl; $R_3$ is hydrogen, or halo, and n is 1 or 2; or a pharmaceutically acceptable salt thereof and a pharmaceutically acceptable carrier therefor.

8. A pharmaceutical formulation of claim 7 wherein the compound is 3-benzyl-8-(methylamino)-1,2,4-triazolo[4,3-a]pyrazine,
3-(2-fluorobenzyl)-8-(methylamino)-1,2,4-triazolo[4,3-a]pyrazine,
8-amino-3-(2-fluorobenzyl)-1,2,4-triazolo[4,3-a]pyrazine,
3-(3-fluorobenzyl)-8-(methylamino)-1,2,4-triazolo[4,3-a]pyrazine,
3-(4-fluorobenzyl)-8-(methylamino)-1,2,4-triazolo[4,3-a]pyrazine,
3-(2,5-difluorobenzyl)-8-(methylamino)-1,2,4-triazolo[4,3-a]pyrazine,
8-amino-3-(2,5-difluorobenzyl)-1,2,4-triazolo[4,3-a]pyrazine,
3-(2,6-difluorobenzyl)-8-(methylamino)-1,2,4-triazolo[4,3-a]pyrazine,
8-amino-3-(2,6-difluorobenzyl)-1,.2,4-triazolo[4,3-a]pyrazine,
8-(cyclopropylamino)-3-(2,6-difluorobenzyl)-1,2,4-triazolo-[4,3-a]pyrazine, or
8-(cyclopropylamino)-3-(2-fluorobenzyl)-1,2,4-triazolo-[4,3-a]pyrazine, or a pharmaceutically acceptable acid addition salt thereof.

9. The pharmaceutical formulation of claim 8 wherein the salt is the hydrochloride salt.

10. A pharmaceutical formulation of claim 9 which is a tablet or capsule.

11. A method of treating a mammal which has been identified as having convulsions which comprises administering a pharmaceutical formulation as defined in claim 7.

12. The method of claim 11 which comprises the oral administration of a tablet or capsule containing
3-benzyl-8-(methylamino)-1,2,4-triazolo[4,3-a]pyrazine,
3-(2-fluorobenzyl)-8-(methylamino)-1,2,4-triazolo[4,3-a]pyrazine,
8-amino-3-(2-fluorobenzyl)-1,2,4-triazolo[4,3-a]pyrazine,
3-(3-fluorobenzyl)-8-(methylamino)-1,2,4-triazolo[4,3-a]pyrazine,
3-(4-fluorobenzyl)-8-(methylamino)-1,2,4-triazolo[4,3-a]pyrazine,
3-(2,5-difluorobenzyl)-8-(methylamino)-1,2,4-triazolo[4,3-a]pyrazine,
8-amino-3-(2,5-difluorobenzyl)-1,2,4-triazolo[4,3-a]pyrazine,
3-(2,6-difluorobenzyl)-8-(methylamino)-1,2,4-triazolo[4,3-a]pyrazine,
8-amino-3-(2,6-difluorobenzyl)-1,2,4-triazolo[4,3-a]pyrazine,
8-(cyclopropylamino)-3-(2,6-difluorobenzyl)-1,2,4-triazolo-4,3-a]pyrazine, or
8-(cyclopropylamino)-3-(2-fluorobenzyl)-1,2,4-triazolo-4,3-a]pyrazine, or a pharmaceutically acceptable salt thereof.

13. The method of claim 11 which comprises the parenteral administration of
3-benzyl-8-(methylamino)-1,2,4-triazolo[4,3-a]pyrazine,
3-(2-fluorobenzyl)-8-(methylamino)-1,2,4-triazolo[4,3-a]pyrazine,
8-amino-3-(2-fluorobenzyl)-1,2,4-triazolo[4,3-a]pyrazine,
3-(3-fluorobenzyl)-8-(methylamino)-1,2,4-triazolo[4,3-a]pyrazine,
3-(4-fluorobenzyl)-8-(methylamino)-1,2,4-triazolo[4,3-a]pyrazine,
3-(2,5-difluorobenzyl)-8-(methylamino)-1,2,4-triazolo[4,3-a]pyrazine,
8-amino-3-(2,5-difluorobenzyl)-1,2,4-triazolo[4,3-a]pyrazine,
3-(2,6-difluorobenzyl)-8-(methylamino)-1,2,4-triazolo[4,3-a]pyrazine,
8-amino-3-(2,6-difluorobenzyl)-1,2,4-triazolo[4,3-a]pyrazine,
8-(cyclopropylamino)-3-(2,6-difluorobenzyl)-1,2,4-triazolo-4,3-a]pyrazine, or
8-(cyclopropylamino)-3-(2-fluorobenzyl)-1,2,4-triazolo-4,3-a]pyrazine, or a pharmaceutically acceptable salt thereof.

14. The method of claim 11 wherein said mammal is a human.

15. A method of treating epilepsy in a human which comprises administering to said human a therapeutically effective amount of
3-benzyl-8-(methylamino)-1,2,4-triazolo[4,3-a]pyrazine,
3-(2-fluorobenzyl)-8-(methylamino)-1,2,4-triazolo[4,3-a]pyrazine,
8-amino-3-(2-fluorobenzyl)-1,2,4-triazolo[4,3-a]pyrazine,
3-(3-fluorobenzyl)-8-(methylamino)-1,2,4-triazolo[4,3-a]pyrazine,
3-(4-fluorobenzyl)-8-(methylamino)-1,2,4-triazolo[4,3-a]pyrazine,
3-(2,5-difluorobenzyl)-8-(methylamino)-1,2,4-triazolo[4,3-a]pyrazine,
8-amino-3-(2,5-difluorobenzyl)-1,2,4-triazolo[4,3-a]pyrazine,
3-(2,6-difluorobenzyl)-8-(methylamino)-1,2,4-triazolo[4,3-a]pyrazine,
8-amino-3-(2,6-difluorobenzyl)-1,2,4-triazolo[4,3-a]pyrazine,
8-(cyclopropylamino)-3-(2,6-difluorobenzyl)-1,2,4-triazolo-4,3-a]pyrazine, or
8-(cyclopropylamino)-3-(2-fluorobenzyl)-1,2,4-triazolo[4,3-a]pyrazine, or a pharmaceutically acceptable salt thereof.

16. A compound of claim 1 wherein $R_3$ is fluoro.

17. A formulation of claim 7 wherein $R_3$ is fluoro.

18. A compound 3-(2-fluorobenzyl)-8-(methylamino)-1,2,4-triazolo[4,3-a]-pyrazine or a pharmaceutically acceptable acid addition salt thereof.

19. A compound of claim 18, wherein the salt is the hydrochloride salt.

20. A pharmaceutically acceptable acid addition salt of 3(2-fluorobenzyl)-8-(methylamino)-1,2,4-triazolo[4,3-a]pyrazine.

21. The hydrochloride salt of 3(2-fluorobenzyl)-8-(methylamino)-1,2,4-triazolo[4,3-a]pyrazine.

22. A method of treating epilepsy in humans, which comprises administering an effective epilepsy treatment amount of the compound or salt of claim 18, 19, 20 or 21 to said human.

23. A pharmaceutical formulation in the form for parenteral or oral use comprising the compound or salt of claim 18, 19, 20 or 21 and a pharmaceutically acceptable carrier therefore.

* * * * *